United States Patent [19]

Shoesmith

[11] Plant 4,326

[45] Oct. 31, 1978

[54] CHRYSANTHEMUM PLANT NAMED PARLIAMENT

[75] Inventor: Leonard H. Shoesmith, Westfield-Woking, England

[73] Assignee: Pan-American Plant Company, West Chicago, Ill.

[21] Appl. No.: 797,381

[22] Filed: May 16, 1977

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new variety of chrysanthemum plant of the spray type characterized by its medium sized blooms of a daisy form which have three to four rows of purple-pink ray florets, by its uniform year around 8 to 9 week response, and by its production of 8 to 13 fully developed flowers on each terminal stem.

4 Drawing Figures

BACKGROUND OF THE NEW PLANT

My new variety of chrysanthemum was discovered by me at Westfield-Woking, Surrey, England, in 1972 as a seedling of unidentified parentage growing among stock greenhouse plants maintained by me for breeding purposes. The dark pink coloring of its daisy formed flowers and the many flowers borne on a strong, tall terminal stem caused me to select this plant for trial and my propagation of this plant at Westfield-Woking by means of cuttings from the original plant and subsequently by vegetative cuttings from the resulting clone demonstrated to me that the novel characteristics of the new plant appeared to be firmly fixed and to hold true from generation to generation.

As a result of my work with this new plant, its propagation by vegetative cuttings is now being done at West Chicago, Ill., and at Cortez, Fla., and my original observations of the distinctive characteristics of the plant have been found to be retained from generation to generation at each location.

DESCRIPTION OF THE DRAWINGS

This new chrysanthemum plant is illustrated by the accompanying drawings, the first of which is a full color photographic print showing a flowering stem of the new plant with buds, foliage and fully opened flowers, the view having been selected to show the manner in which the flowers are carried on the main stem. The colors shown are as nearly true as it is reasonably possible to obtain by conventional photographic procedures, the plant shown being one flowered at West Chicago, Ill., in Sept. 1976. The second sheet of drawings is a mechanical reproduction of a photocopy of typical leaves of the new plant taken from a single flowering stem to show the leaves at several stages of maturity.

DESCRIPTION OF THE NEW PLANT

The following is a detailed description of my new variety of chrysanthemum with color designations according to the R.H.S. Colour Chart published by The Royal Horticultural Society of London, England.

THE PLANT

Origin: Seedling.

Parentage: Unidentified, this plant having been found among random pollinated greenhouse plants.

Classification:

*Botanic.*—*Chrysanthemum morifolium.*

*Commercial.*—Greenhouse cut flower.

Form: Herbaceous bush.

Height: 2 to 3½ feet.

Growth: Terminal and upright, with low to moderate vigor and sturdy stems of good strength.

Branching: Normal, under natural conditions.

Foliage: Abundant, averaging six to eight leaves per 6 inches of stem.

*Leaf size.*—For average mature leaf — length 3 to 4¾ inches; width 2 to 3⅝ inches.

*Leaf shape.*—Lanceolate, lobed and deeply serrated.

*Color.*—Upper side — very dark Green, 147A. Under side — dark Green, 147B.

*Surface texture.*—Canescent.

*Venation.*—Pinnate.

THE BUD

Form: Globular.

Size:

*Diameter.*—5/16 to ⅜ inch.

*Depth.*—¼ inch.

Opening: Slowly. Flowering occurs several weeks after Phyllaries begin to divide.

Color:

*When phyllaries first divide.*—Yellow Green, 144A.

*When florets begin to unfurl.*—Red-Purple, 64A.

Phyllaries: The outside of the receptacle bears many involucral bracts.

*Form.*—Spear-shaped and upstanding.

*Surface texture.*—Pubescent.

*Color.*—Inside and outside — very dark Green, 147A.

Peduncle: Erect and sturdy.

*Length.*—¼ to ⅝ inch.

*Surface texture.*—Pubescent.

*Color.*—Dark Green, 147B.

THE FLOWER

Flowering season: This plant can be flowered the year around with photoperiod control.

*Natural.*—About October 25 to November 2.

*Recommended.*—Year around.

Response: 8 to 9 weeks.

Blooms:

*Flower type.*—Composite, single and of daisy form, each comprising a head of many florets borne on a receptacle.

*Borne.*—As a spray of relatively long racemose stems each terminated by a single composite capitulum.

*Size.*—Medium. Diameter: 2½ to 3 inches. Depth: ½ to ¾ inch.

*Shape.*—Flat when bloom first opens, changing later by a slight reflexing of the ray florets.

*Florets.*—40 to 52 in number, arranged in three to four rows. Form: Linear with obtuse apex. Length: 1¼ to 1½ inches. Width: ⅜ inch. Texture: Of medium firmness. Appearance: Very slight shine.

Color:

| Outer Florets | Jan. | Feb. | March | Apr. | May | June to Oct. | Dec. |
|---|---|---|---|---|---|---|---|
| Upper Side | 66C | 70B | 71C & D 68A & B | 70A | 70A | 74C | 74C |
| Reverse | 68D | 69A | 68C & D | 70C | 74D | 73D | 78D |

Color change: Moderate fade under high light conditions.

Persistence: Florets hang on and dry.

Fragrance: Typical chrysanthemum.

Lasting quality:

*On plant.*—2 to 3½ weeks.

*As cut flower.*—6 to 14 days.

REPRODUCTIVE ORGANS

Stamens: five in syngenesious arrangement.

*Filaments.*—1/16 to ⅛ inch long. Color: Light Yellow

*Pollen.*—Color — Yellow.

Pistils: Number — one to each ray and disc floret.

*Styles.*—⅛ to 3/16 inch long.

*Stigmas.*—Color — Yellow.

Ovaries: Inferior and bicarpellate.

My new cultivar of spray chrysanthemum is distinguished by its daisy flower form with three or four rows of purple-pink ray florets which provide medium sized, 2½ to 3 inch diameter blossoms which have light to moderate pollen production. This plant has a uniform year around 8 to 9 week flowering response, producing 8 to 13 fully developed blooms on each terminal stem, with good stem strength and dense, glossy, dark green foliage.

I claim:

1. A new and distinct chrysanthemum cultivar substantially as herein shown and described, distinguished by its medium sized daisy-form blooms which have three to four rows of purple-pink ray florets, by its uniform 8 to 9 week year around flowering response, and by its ability to produce as many as 13 fully developed flowers on each terminal stem.

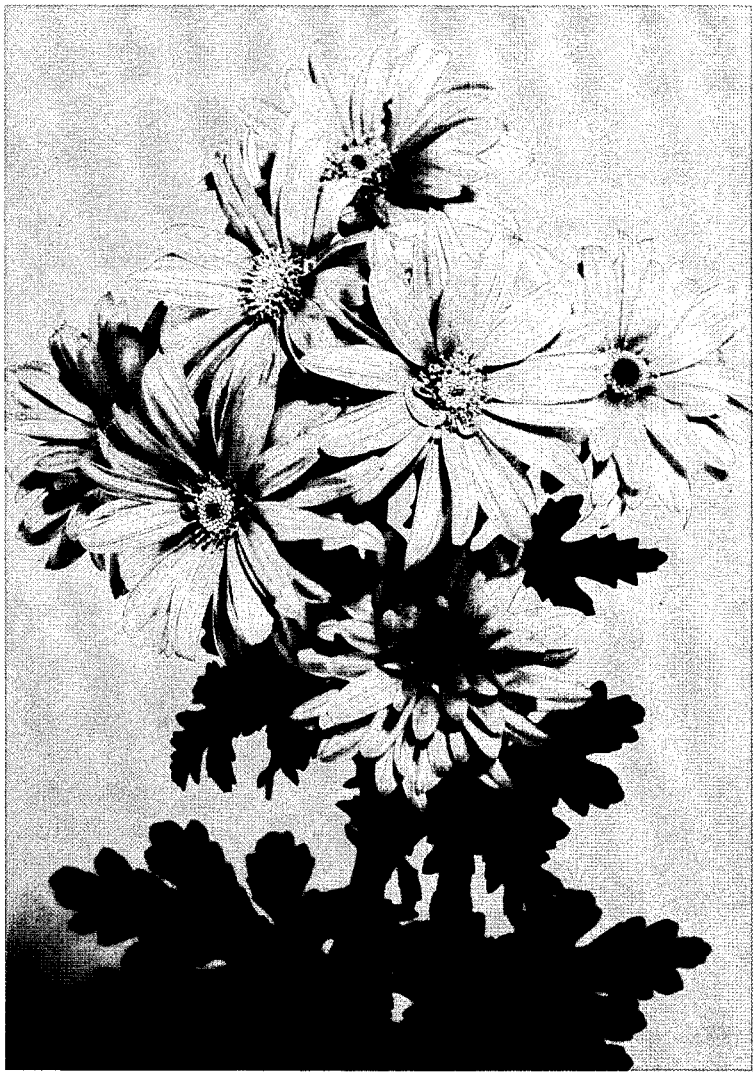

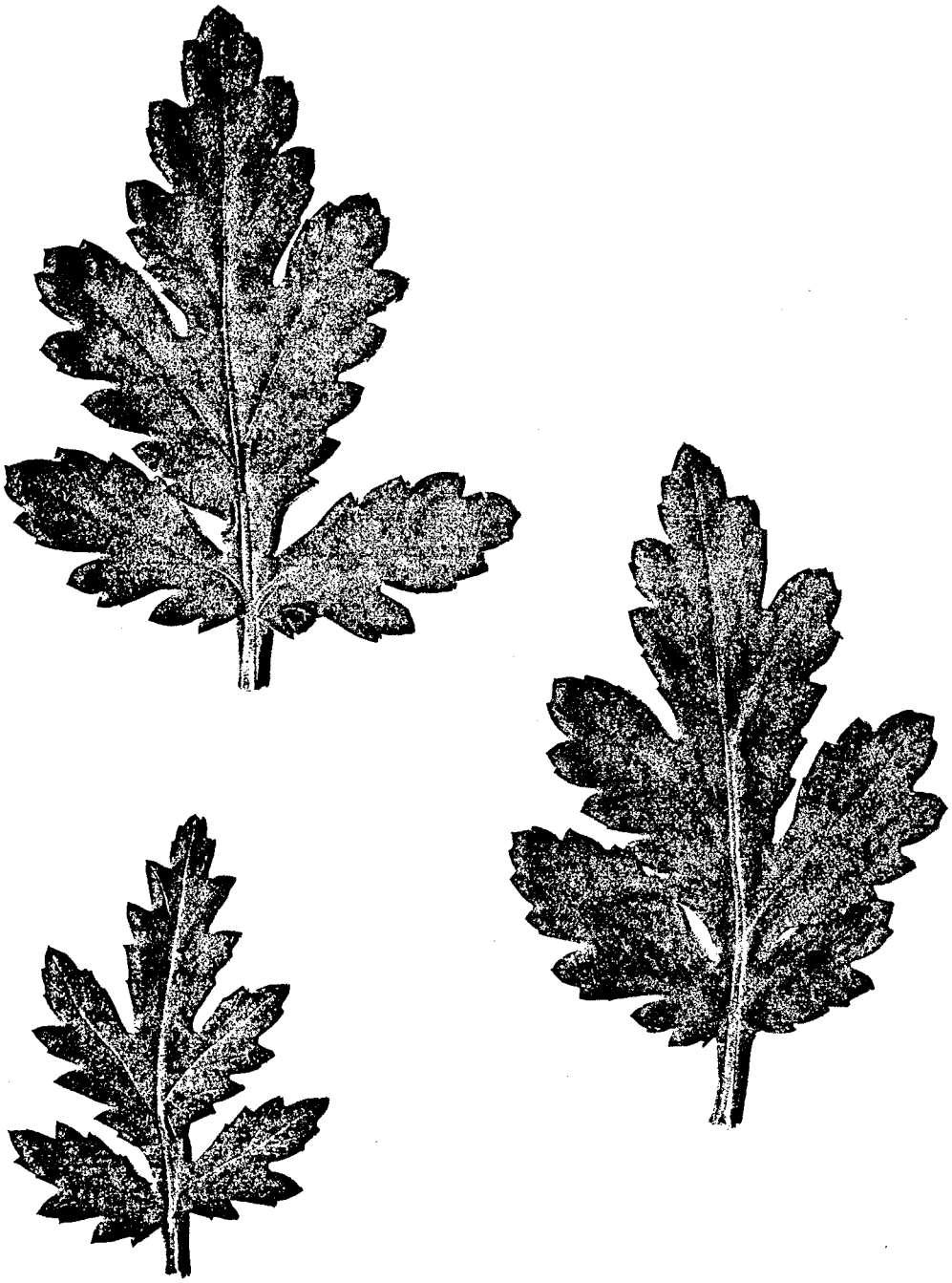

* * * * *